(12) United States Patent
Lopez et al.

(10) Patent No.: US 8,779,203 B2
(45) Date of Patent: Jul. 15, 2014

(54) CONTINUOUS PRODUCTION OF ARYLAMINE

(75) Inventors: Karina Lopez, Richmond Hill (CA); Santiago Faucher, Oakville (CA); Marko Saban, Toronto (CA); Rosa Duque, Brampton (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/213,907

(22) Filed: Aug. 19, 2011

(65) Prior Publication Data

US 2013/0046110 A1 Feb. 21, 2013

(51) Int. Cl.
*C07C 211/00* (2006.01)

(52) U.S. Cl.
USPC .......................................... 564/309

(58) Field of Classification Search
None
See application file for complete search history.

(56) References Cited

U.S. PATENT DOCUMENTS

| | | | |
|---|---|---|---|
| 6,958,204 B2 * | 10/2005 | Tanaka et al. | 430/133 |
| 7,563,932 B2 | 7/2009 | Coggan | |
| 7,767,856 B2 | 8/2010 | Bender | |
| 2009/0149675 A1 * | 6/2009 | Coggan et al. | 564/309 |

* cited by examiner

*Primary Examiner* — Clinton Brooks
(74) *Attorney, Agent, or Firm* — MDIP LLC

(57) ABSTRACT

A process for forming arylamines by continuous Buchwald-Hartwig reaction using, in part, a plug flow reactor with a fluid flow path greater than about 1 mm in diameter and a single solvent under pressure to form a product with a space time yield of at least 100 g/L/hr.

10 Claims, No Drawings

CONTINUOUS PRODUCTION OF ARYLAMINE

FIELD

The disclosure relates to a continuous reaction scheme for producing arylamines, such as, dialkoxy tetraphenylbenzidines, for example, dimethoxy tetraphenylbenzidine, in efficient and high yield using a certain plug flow reactor.

BACKGROUND

Arylamines are useful as hole transport compounds in electrophotographic imaging devices and processes, see, for example, U.S. Pat. No. 7,544,842, incorporated herein by reference in entirety. Dimethoxy tetraphenylbenzidine (also known as, for example, N,N'-diphenyl-N,N'-bis(3-methoxylphenyl)-[1,1'-biphenyl]-4,4'-diamine or N,N'-diphenyl-N, N'-bis(3-methoxylphenyl)-[4,4'-diaminobiphenyl]) is a precursor of the hole transport material, dihydroxy tetraphenylbenzidine (also known as N,N'-diphenyl-N,N'-bis (3-hydroxyphenyl)-[1,1'-biphenyl]-4,4'-diamine), which is readily produced from dimethoxy tetraphenylbenzidine. Dihydroxy tetraphenylbenzidine can be used in one or more layers of photoreceptors, see, for example, U.S. Pat. No. 5,336,577 which teaches use of dihydroxy tetraphenyl benzidine in a single layer photoreceptor. Tetraphenyl benzidine-containing polymers are described in U.S. Pat. Nos. 4,801, 517, 4,806,443, 4,806,444, 4,818,650, 4,871,634, 4,935,487, 4,956,440 and 5,028,687, the disclosures thereof are incorporated herein by reference in entirety.

Synthesis of arylamine hole transport compounds generally requires intermediates, some of which are costly and/or are time-consuming to produce, that are part of multi-step processes.

Buchwald chemistry can be used to produce arylamine compounds. The formation of diarylamines and triarylamines comprises an exothermic reaction of an arylamine with an aryl halide in the presence of a palladium catalyst and base.

Many of those synthesis methods are batch reactions. Because of the reaction conditions, scaling of batch Buchwald syntheses presents challenges, such as, accommodating the heat of reaction and batch workup delays.

A continuous process, if possible, provides advantages over more conventional batch reactions by providing one or more of faster efficient mixing, selectivity enhanced-side products, reduced secondary reactions, higher yield, fewer impurities, extreme reaction conditions, time and cost savings, and increased surface area to volume ratio that results in good mass and heat transfer.

Microreactors and minireactors for making particular arylamines under certain conditions have been described. However, the smaller bore fluid channels used therein may limit production, scaling and reaction efficiency. U.S. Pat. No. 7,563,932 describes a microreactor, and is incorporated herein by reference in entirety.

Continuous processes however, do have some shortcomings, for example, because of the need for reactant and product communication means, there is a risk of blocking such conduits with reactants and/or products. Hence, reactions that produce a solid product or side product, such as, solid halide salts, such as, sodium bromide, produced in a Buchwald reaction, may not be amenable to a continuous process.

SUMMARY

The disclosure addresses those and other needs by providing an improved continuous plug flow reactor system under controlled temperature and pressure for preparing arylamines at high rate, at high yield or both, for example, dimethoxy tetraphenylbenzidine. Hence, for example, 3-methoxy diphenylamine can be reacted with dibromobiphenyl in the presence of dichloro bis(di-tert-butylphenylphosphine)palladium (II) and sodium tert-pentoxide in a single solvent system comprising toluene. Reactants can be fed from one or more reservoirs continuously or metered, optionally combined in a mixing vessel, at controllable rates and in controllable amounts by communicating devices, such as, lines, conduits, tubing and so on with a smallest internal dimension or diameter of greater than about 1 mm. The optional mixing vessel can comprise a heating element. The mixture can be transported to a reaction site or a reactor by such communicating devices. The mixture can be heated during that transit. The reactor can comprise a series of parallel tubes, channels, voids, tubular voids, voids within partially flattened or ovoid tubes and the like with a smallest internal dimension or diameter of greater than about 1 mm, that are connected to provide a continuous directed flow path through the reactor. The reactor can comprise a heating element, which can comprise a liquid, such as, an oil, that bathes the directed parallel flow path to provide the appropriate temperature under which the reaction occurs. The flow path can be connected to an egress device, such as, said communication devices, such as, a line, conduit, tubing and the like to course the reaction mixture to a product receiving vessel. In embodiments, the product receiving vessel is maintained under pressure. The egress device can be temperature controlled to enable a rapid cooling of the reaction mixture. The reaction apparatus can be operated under pressure to reduce reagent and solvent boiling points and to ensure unimpeded movement of the reaction mixture through the reactor.

That combination of reactants, methods and apparatus provides a continuous method for producing, for example, dimethoxy tetraphenylbenzidine, at high rate and in a high yield, cost effective manner, that is, for example, the desired product can be obtained at levels at least 100 times greater per liter of reaction mixture per hour than is obtained using conventional batch processes.

DETAILED DESCRIPTION

In this specification and the claims that follow, singular forms such as "a," "an," and "the" include plural forms unless the content clearly dictates otherwise.

Unless otherwise indicated, all numbers expressing quantities and conditions, and so forth used in the specification and claims are to be understood as being modified in all instances by the term, "about." "About," is meant to indicate a variation of no more than 20% from the stated value. Also used herein is the term, "equivalent," "similar," "essentially," "substantially," "approximating" and "matching," or grammatic variations thereof, have generally acceptable definitions or at the least, are understood to have the same meaning as, "about."

"Connection," or grammatic forms thereof is used herein to encompass means or devices for communicating, transporting, connecting and so on two or more devices, such as, vessels, which can be, for example, a pipe, a tube, a tubing, a hose, a conduit, a straw and so on, any device that enables the movement a fluid therein from one device to another, such as, from one vessel to another. Thus, an example of a connecting device is a tubing, which can be made of a plastic, a metal and so on.

A, "plug flow reactor," as used herein refers to a heat exchange conducive arrangement of connections within which a fluid is in communication and within which a reaction occurs. Hence, for example, a metal tubing, which may be coiled and so may comprise a plug flow reactor. A plug flow reactor can be contained in a vessel, for example, the vessel can serve as a heat sink or as a means for controlling the temperature of the reactor and the reaction within.

The term, "alkyl," refers, for example, to a branched or unbranched saturated hydrocarbon group, derived from an alkane and having the general formula $C_nH_{2n+1}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. "Halogenated alkyl" refers, for example, to an alkyl group in which at least one hydrogen atom, and optionally all hydrogen atoms, is replaced by a halogen atom.

The term, "aryl," refers, for example, to monocyclic or polycyclic structures, which can be bridged or fused (i.e., rings which share adjacent pairs of carbon atoms). An aryl of interest is a carbocyclic aromatic ring system having about 6 to about 20 carbon atoms or more, such as phenyl, naphthyl, anthrycyl and the like. Optionally, an aryl may be substituted with one or more independently selected substituents, including alkyl, alkenyl, alkoxy, hydroxyl, nitro, further aryl groups, halogen, alkoxy groups, such as, methoxy, ethoxy and so on. To facilitate production of a dimethoxy tetraphenylbenzidine, an aryl can be substituted with a methoxy group.

The term, "arylamine," refers, for example, to moieties containing both plural aryl groups and an amine group. Exemplary aralkylene groups have the structure, Ar-NRR', in which Ar represents an aryl group, R is an aryl and R' is a group that may be selected from hydrogen and substituted or unsubstituted alkyl, alkenyl, aryl and other suitable functional groups. Ar or R can comprise an alkoxy group, such as, a methoxy group, an ethoxy group and so on.

The terms, "standard temperature," and, "standard pressure," refer, for example, to the standard conditions used as a basis where properties vary with temperature and/or pressure. Standard temperature is 0° C.; standard pressure is 101,325 Pa or 760.0 mmHg. The term, "room temperature," refers, for example, to temperatures in a range of from about 20° C. to about 25° C.

The terms, "one or more," and, "at least one," herein mean that the description includes instances in which one of the subsequently described circumstances occurs, and that the description includes instances in which more than one of the subsequently described circumstances occurs.

An improved process for producing an arylamine, such as, a dialkoxy tetraphenylbenzidine, such as, a dimethoxy tetraphenylbenzidine, is described which can occur under controlled pressure in a closed system in continuous fashion by reacting an aryl halide, such as, an aryl dihalide, such as, a biaryl dihalide, such as, a biphenyl dihalide, such as, dibromobiphenyl, with an arylamine, such as, a diphenylamine, in embodiments, an alkoxy diphenylamine, such as, a methoxy diphenylamine, such as, 3-methoxy diphenylamine, in the presence of a palladium catalyst, such as, dichloro bis(di-tert-butylphenylphosphine)palladium (II), such as, Pd-122, (Johnson Matthey Catalysis & Chiral Technologies, NJ) and a base, such as, a sodium t-pentoxide, in a single solvent system comprising a single organic solvent, such as, toluene, in a plug flow reactor comprising fluid communicating and transport means and devices having a smallest inside dimension or a diameter greater than about 1 mm, greater than about 1.5 mm, greater than about 2 mm, greater than about 2.5 mm or larger. The fluid communication and transport means and devices can have a smallest inside diameter or a diameter greater than about 20 mm, greater than about 25 mm, greater than about 30 mm or larger.

The aryl halide can be any suitable aryl halide to produce the product of interest, such as, dimethoxy tetraphenylbenzidine. The halide group can be fluoride, chloride, bromide, iodide or astatide. Thus, for example, the aryl halide can be a bridged biaryl moiety, such as, 4-bromobiphenyl, or can comprise a halogen on each aryl group.

The arylamine reagent can be any suitable arylamine that when reacted with the halide will produce the arylamine product of interest, such as, dimethoxy tetraphenylbenzidine. A suitable arylamine can be a biarylamine, such as, a dimethoxybiarylamine. The amine group can comprise a hydrogen or other group for reaction with the halogen, and is one which produces a soluble side product or a side product that is soluble or which comprises finely divided particles that remain suspended in the medium or solvent to provide a substantially flowable suspension under the reaction conditions of interest, such as, under pressure, and at room temperature or higher. One aryl of a diarylamine comprises an alkoxy group, such as, a methoxy group.

The reaction comprises a suitable catalyst. Although not particularly limited, suitable catalysts are those that are known or discovered to be useful for formation of nitrogen-carbon bonds. For example, suitable catalysts include ligated palladium catalysts, such as those disclosed in, for example, J. Org. Chem. 2000, 65, 5327-5333, the entire disclosure of which is incorporated herein by reference. It will be apparent to those skilled in the art that ligands, such as, any tertiary phosphine ligand, such as, biaryldialkylphosphine or trialkyl phosphine ligands, or N-heterocyclic carbene complexes could be used to produce suitable results (from the point of view of conversion, soluble products and yield), and thus would be suitable to ligate palladium or other metals and thus act as catalysts for the process described herein. In embodiments, an unexpected example of a catalyst is dicholoro bis (di-tert-butylphenylphosphine)palladium (II), such as, Pd-122 (Johnson Matthey Catalysts, NJ), which is not listed by the manufacturer as a catalyst suitable or recommended for a Buchwald reaction.

A suitable base that may be used includes an alkaline hydroxide, an alkaline alkoxide, a silanolate, such as, sodium trimethylsilanolate or potassium trimethylsilanolate, and the like. Other bases that may be used include those having the general formula, MOR, in which O is oxygen, M is a metal atom and R is hydrogen or an alkyl group. M is selected from potassium, sodium, lithium, calcium, magnesium and the like; and R is a hydrogen or a straight or branched alkyl group selected from, for example, methyl, ethyl, propyl, butyl, pentyl, hexyl, heptyl, octyl, nonyl and decyl. Suitable other bases include potassium tert-butoxide, sodium tert-butoxide and sodium tert-pentoxide.

The reaction is carried out in a suitable single species of solvent, such as, an organic solvent or liquid, such as, toluene, decane, other hydrocarbon solvents (either aromatic or saturated hydrocarbons), 1,3-dioxolane, trihexyl(tetradecyl) phosphonium saccharin (Saccarin IL), xylene, pentane, dioxane, hexane, ethers, such as, tetrahydrofuran and dimethoxyethane, alcohols, such as, butanol, hexanol and so on, and trihexyl(tetradecyl)phosphonium bis(trifluoromethylsulfonyl)amide (IL-109). Unexpectedly, a mixture of solvents to solubilize any side products or byproducts is not needed and a single solvent, such as, toluene, can be used in the practice of the disclosed method.

The choice of reactants is directed not only to efficiently attaining maximal yield and purity, but also to obtain soluble product and side products, products or side products that are soluble or form smaller particulates that do not aggregate or agglomerate, and/or solvent and mixtures that retain low viscosity throughout the reaction under pressure and at room temperature, that is, are substantially flowable under the operating and collecting conditions.

The reaction can be conducted under an atmosphere of inert gas (such as nitrogen or argon) so as to minimize or to preclude deactivation of catalyst and/or base by, for example, oxygen or moisture.

The reactor is operated under pressure and optionally the product can be collected in a vessel also under pressure. Generally, a suitable pressure is one above a floor defined by the boiling point of the solvent(s). Hence, the operating pressure can be one above the pressure at which the phases in the reactor coexist in equilibrium. Because pressure varies with temperature, the operating pressure can be selected based on the operating temperature of the reaction. Suitable pressures can be greater than about 6 bar, greater than about 7 bar, greater than about 8 bar, or greater, but no more than about 22 bar, no more than about 23 bar, no more than about 24 or no more than about 25 bar.

Reagents can be introduced using pumps which enable graded or metered introduction of reactants and which maintain the reaction environment, such as, the reactor and the receiving vessel, under pressure.

The assembly or apparatus that can be used generally comprises parts and components known in the art, and reference can be made to the teachings of U.S. Pat. Nos. 7,563,318, 7,563,932 and 7,767,856, herein incorporated by reference in entirety.

Tubing, lines, conduits and other connections, transporting devices or communication devices are used to interconnect and to transport the materials from reservoirs to a vessel, from a vessel to a vessel, from a vessel to a reactor and so on. Reagents can be maintained in interconnected reservoirs, and the product collected in an interconnected receiving vessel. In embodiments, the reaction occurs in a tubing, line, conduit, flattened tube and the like to provide ongoing contact amongst the reactants, and fine temperature and pressure control for the reaction to occur and to accommodate the produced heat. Such connections can be of any material suitable to withstand the temperatures and pressures used, as well as the reagents. Thus, for example, a connection or connecting device can comprise a metal, such as, stainless steel, a plastic and so on. The size of the connections is a design choice, and relates in part, for example, to the projected amount of product desired and the desired temperature control. Hence, the fluid communicating and transport means and devices, and the connections have a smallest inside dimension or a diameter greater than about 1 mm, greater than about 1.5 mm, greater than about 2 mm, greater than about 2.5 mm or larger. The fluid communication and transport means and devices, and the connections have a smallest inside diameter or a diameter greater than about 20 mm, greater than about 25 mm, greater than about 30 mm or larger. The material is one which is conductive to heat to permit rapid transfer of heat into and out of the connection. In embodiments, reactor volume is less than about 40 ml, less than about 30 ml, less than about 20 ml, less than about 10 ml.

The apparatus can include an optional mixing vessel where the reactants in whole or in part can be combined into a homogenous mixture, emulsion and so on prior to reaction. Hence, reagents are fed into a mixing vessel and then the mixture is communicated to the reactor. In embodiments, the mixed ingredients are heated prior to being introduced into the reactor. In embodiments, individual feed streams of reactants can merge into a single communication device containing a mixture of reactants for producing arylamine. In embodiments, the feeds merge in the reactor. In embodiments, such a mixture in a communication device can be heated.

The reaction occurs in a void or space that is exposed to a high surface area to volume ratio to allow fine temperature control, such as a connection as provided herein. Hence, the mixed reactants can be communicated in a connection which then is exposed to the appropriate temperature to enable the reaction to occur. In embodiments, a conduit of interest is configured to form interconnected substantially parallel pathways, such as a coil and so on as known in the heat exchange art to provide increased volume and ample heat exchange for the reaction to occur. The reaction site and the interconnected substantially parallel pathway can be centralized in a vessel, a reactor, which can comprise an enclosure of the interconnected parallel pathways and the like, which vessel can contain a medium, such as, a liquid, as a bath for conducting heat, such as, an oil.

To facilitate the reaction and to enhance efficiency and yield, portions of the reaction apparatus comprise heating elements. For example, the mixing receptacle can comprise a heating element to enable raising the temperature of the mixed reagents. The mixed reagents are transported from a mixing receptacle to a reactor which can comprise a vessel that comprises, for example, a heating element or heated fluid, as a bath. The conduit transporting the mixture can comprise a heating element so that the reactants are heated in transit so as to be nearer to the reaction temperature when introduced into the reactor.

The temperature of the vessels generally will lie within from about room temperature to about 200° C. or as needed to enable the reaction to occur. The streams containing the reactants and other necessary inputs or outputs can also be fed or transported at different temperatures, for example a stream may be heated to about 40° C., to about 60° C., to about 80° C. The reaction can occur at a temperature of from about room temperature to about 200° C., from about 40° C. to about 190° C., from about 50° C. to about 180° C., from about 60° C. to about 170° C. Because of the greater surface area to volume ratio of the reactor, heat dissipation and transfer occur readily for the exothermic reaction. The exotherm also can minimize the amount of heat that is introduced into the reactor.

As mentioned, the reaction can be carried out at pressures higher than atmospheric pressure, dictated, for example, by the solvent(s) used and the operating temperature. For example, the operating pressure can be more than about 125 psi, more than about 150 psi, more than about 175 psi, more than about 200 psi or higher but no more than about 300 psi, no more than about 275 psi, no more than about 250 psi. Not wanting to be bound by theory, it is believed the controlled pressure ensures continual movement of fluids and suspensions through the reactor, and provides the observed enhanced reaction efficacy and enhanced product yield.

Under flow conditions, the reaction time can be less than about 20 min, less than about 17 min, less than about 15 min.

The residence time necessary in the method according to the invention depends on various parameters, such as, for example, the temperature or reactivity of the starting materials, the length of the transporting device or conduits, the length of the conduits in the reactor, the viscosity of the solutions, the fluid pressures used, the back pressures formed by a vessel and so on. The term "residence time" refers to the internal volume of the reaction zone within the apparatus occupied by the reactant fluid flowing through the space divided by the average volumetric flow rate for the fluid flowing through the space, at the temperature and pressure being used. The residence time may be, for example, between about 5 min and about 20 min, between about 10 min and about 15 min. In embodiments, the residence time can be less than about 5 min, less than about 4 min, less than about 3 min, less than about 2 min, less than about 1 min.

A measure of reaction efficiency is the metric, space-time yield (STY) expressed in grams/liter/hour. The greater the value, the more efficient and productive the method as greater amounts of product are obtained per unit volume of reaction mixture per unit time. A continuous process of interest can produce an STY of at least about 100 g/l/hr, at least about 200 g/l/hr, at least about 300 g/l/hr, at least about 400 g/l/hr or more. As compared to a batch process, examples of which appears below, a continuous process of interest can produce an STY at least about twice as great, at least about three times as great, at least about four times as great or more that what is observed for a batch process.

Another metric of reaction efficiency is rate product, expressed as weight of product per unit time. The reaction of interest has a product rate of at least about 0.6 g/min, at least about 0.7 g/min, at least about 0.8 g/min, at least about 0.9 g/min, at least about 1.0 g/min.

After the reaction is completed, suitable separation, filtration, and/or purification processes can be conducted, as desired to a desired purity level. For example, the desired arylamine can be subjected to conventional organic washing steps, can be separated, can be decolorized (if necessary), treated with known absorbents (such as silica, alumina and clays, if necessary) and the like. The final product can be isolated, for example, by a suitable recrystallization procedure. The final product can be dried, for example, by air drying, vacuum drying, or the like. All of these procedures are conventional and will be apparent to those skilled in the art.

The arylamine produced by the continuous process can be further processed and/or reacted to provide other compounds for separate use, such as, dihydroxy tetraphenylbenzidine, for use in electrophotographic applications, such as, an imaging member.

Specific examples are described in detail below. The examples are intended to be illustrative, and the materials, conditions, and process parameters set forth in the exemplary embodiments are not limiting. All parts and percentages are by weight unless otherwise indicated.

EXAMPLES

The synthesis of an exemplary arylamine, dimethoxy tetraphenylbenzidine, takes place by reacting 3-methoxy diphenylamine, dibromobiphenyl, (t-Bu$_2$PhP)$_2$)PdCl$_2$ and sodium tert-pentoxide in toluene.

All materials used were chemical grade. Dibromobiphenyl and 3-methoxy diphenyamine were purchased from King Chem, China. Anhydrous toluene, 99.8%, and sodium tert-pentoxide, 95%, were purchased from Sigma-Aldrich. The catalyst, Pd-122, was purchased from Johnson Matthey Catalysts, NJ. All materials were used as received. HPLC calibration curves were performed for all the chemicals.

Comparative Batch Reaction

A control batch experiment was performed. Dibromobiphenyl (5.00 g), 3-methoxy diphenylamine (6.55 g), sodium tert-pentoxide (3.88 g) and Pd-122 (0.05 g) were added to a 100 mL round bottom flask. The flask was connected to a reflux column and purged with 5 cycles of vacuum and argon. The flask was kept in argon atmosphere and 40 mL of fresh anhydrous toluene were added to the flask by syringe. The flask was lowered into an oil bath rested on a stir plate. Heating and stirring were started. Temperature of the reaction and oil bath were monitored using resistance probes. Samples were withdrawn at different time intervals and analyzed using HPLC.

Results for the control experiment showed that 96% of the 3-methoxy diphenylamine were converted to dimethoxy tetraphenylbenzidine in 3.8 hrs of reaction (start time began when the reaction mixture attained a temperature of 90.6° C.)

Plug Flow Continuous Process

The experimental continuous set up comprised a syringe pump (ISCO, model 500D, flow rate range 0.001-204 mL/min, flow rate accuracy 0.5% of set point, pressure range 10-3750 psi), two 300 mL high-pressure vessels (Parr Instruments), one stir plate with temperature control, an oil bath (Exceltherm heat transfer fluid) and ball valves (Swagelok). Connections and fittings were 0.125 in outside diameter (OD) stainless steel with 0.028 in wall thickness.

One Parr vessel was used as a mixing vessel and the other was used as a product receiving vessel. The Parr laboratory vessel for mixing purposes was equipped with a magnetic drive for the internal shaft and impeller. Also, the cylinder of the mixing vessel has a bottom port hole to serve as a point of egress to enable delivery of the reaction mixture to the plug flow reactor.

The experimental set up and the operator were protected from unexpected overpressure by safety rupture discs on both Parr vessels. Both reactor vessels have a removable head and sealing was provided using a PTFE gasket with a split ring closure with bolts. Also, both reactor vessels were equipped with vent valves in the removable heads. Pressure was monitored in each Parr vessel using pressure gauges.

The tubular reactor was made using a 0.125 in OD SS tubing with 0.028 in wall thickness. The tubing was folded to form interconnected parallel courses. The length of the tubular reactor is 245 cm. The reactor volume was calculated and found to be around 5.9 mL.

A 5 cm length of Teflon tubing (Chem Glass, ⅛ in., ID 0.062 in, T$_{max}$=200° C. and P$_{max}$=500 psi) was used at the bottom of the mixing vessel (bottom port hole) and before the inlet to the product vessel (removable head) to determine flow rates. Flow rates were determined using a stopwatch and by measuring the volume of the product in the product vessel using a graduated cylinder after completion of the experiment. The Teflon tubing was connected using a bore-through fitting with one end above the bottom of the mixing vessel to prevent settling of solid material at the bottom of the vessel to prevent clogging of the tubing.

The apparatus was at room temperature except for the tubular reactor which was submerged in the oil bath. A resistance probe was used to monitor the oil bath temperature.

In a typical experiment, dibromobiphenyl (15 g), 3-methoxy diphenylamine (19.64 g), sodium tert-pentoxide (11.65 g) and Pd-122 (0.15 g) were added to the mixing vessel. Then, the vessel was sealed using the split ring and bolts. The Parr laboratory vessel was placed in a stand and purged 5 times with cycles of vacuum and nitrogen. Fresh anhydrous toluene (120 mL) was added to the mixing vessel through one of the ports in the head of the vessel. The mixing vessel then was connected to the magnetic drive. Nitrogen was blown from the product line to avoid any deposit of solids in the dead space of the ball valve attachment on the bottom port hole of the mixing vessel (0.125 in tubing and ball valve). Stirring was started at room temperature in a nitrogen atmosphere and left overnight.

A 1 mL sample was drawn from the mixing vessel for HPLC analysis. That concentration was considered as the initial concentration at time 0. The syringe pump was previously refilled at the desired pressure and set at the desired flow rate. Then, the system was pressurized at 150 psi. The reaction mixture was permitted to flow from the mixing vessel to the product vessel through the tubular reactor which was heated in an oil bath. Flow rate was determined using a stop watch and by measuring the volume in the product vessel at the end of the experiment. Sample was taken from the product vessel for HPLC analysis.

A reaction in continuous mode was run at 168° C. and 149 psi (10 bars). The total volume of the mixing vessel, approximately 136 mL, was flowed through the 5.9 mL tubular reactor at an average flow rate of 10.6 mL/min.

After completion of the run, a sample was taken from the product vessel and analyzed by HPLC. The analysis of the amount of reactant and product indicated a conversion to dimethoxy tetraphenylbenzidine of 66%. Under those run conditions, residence time in the reactor was calculated to be 0.56 min. Concentration of dimethoxy tetraphenylbenzidine in the product vessel was 0.12 g/mL. That translates to a production rate of dimethoxy tetraphenylbenzidine of 1.23 g/min.

Table 1 shows a comparison of the control bench top batch experiment (100 mL batch reactor) and the continuous system (5.9 mL tubular reactor). For the calculations, a volume of 55 ml was used for the control batch experiment. As can be seen from the data in the table, the synthesis of dimethoxy tetraphenylbenzidine is about 250 times higher with the continuous system as compared to the batch reaction.

TABLE 1

Comparison of the dimethoxy tetraphenylbenzidine synthesis using different processes

| Parameter | Batch | Continuous |
|---|---|---|
| Reactor Volume | 100 mL | 5.9 mL |
| Reaction Mixture Volume | 55 mL | 156 mL |
| Reaction Time | 230 min | 13 min |
| Conversion (dimethoxy tetraphenylbenzidine % Area) | 96 | 66 |
| Rate dimethoxy tetraphenylbenzidine (g/min) | 0.04768 | 1.23 |
| Space-time yield (g/L/hr) | 52 | 12500 |

All references cited herein are herein incorporated by reference in entirety.

It will be appreciated that various of the above-disclosed and other features and functions, or alternatives thereof, may be desirably combined into many other different systems or applications. Also various presently unforeseen or unanticipated alternatives, modifications, variations or improvements therein may be subsequently made by those skilled in the art, which are also intended to be encompassed by the following claims. Unless specifically recited in a claim, steps or components of claims should not be implied or imported from the specification or any other claims as to any particular order, number, position, size, shape, angle, color or material.

We claim:

1. A process for producing a dimethoxy tetraphenylbenzidine product by a continuous reaction comprising continuously reacting a 3-methoxy diphenylamine reactant dibromobiphenyl, a base and a palladium catalyst, wherein the continuous reaction is carried out in a single species of organic solvent and in a device comprising a continuous fluid conduit, and collecting said dimethoxy tetraphenylbenzidine product continuously so produced, wherein a conversion of the 3-methoxy diphenylamine reactant to the dimethoxy tetraphenylbenzidine product is at least about 50%.

2. The process of claim 1, wherein said catalyst is dicholoro bis(di-tert-butylphenylphosphine)palladium (II).

3. The process of claim 1, wherein said base comprises sodium tert-pentoxide.

4. The process of claim 1, wherein said single solvent species is toluene.

5. The process of claim 1, wherein said reacting is under an atmosphere of inert gas.

6. The process of claim 1, wherein said reacting is at a temperature between about room temperature to about 200° C.

7. The process of claim 1, wherein said dimethoxy tetraphenylbenzidine product is produced at a space-time yield of at least about 100 g/L/hr.

8. The process of claim 1, wherein said dimethoxy tetraphenylbenzidine product is produced in a reaction time of less than about 17 min.

9. The process of claim 1, wherein said dimethoxy tetraphenylbenzidine product is produced at a space-time yield of at least about 100 times greater than a batch reaction.

10. The process of claim 1, wherein said dimethoxy tetraphenylbenzidine product is produced at a rate product of at least about 0.6 g/min.

* * * * *